United States Patent [19]

Butler et al.

[11] 3,990,947

[45] Nov. 9, 1976

[54] COMPOSITION FOR DETECTING FIBRINOGEN, FIBRINOGEN SPLIT PRODUCTS AND FIBRIN SPLIT PRODUCTS

[75] Inventors: James R. Butler, Parsippany; Walter E. Jacobson, Morris Plains; Donald Paul Kronish, Rockaway; James E. Turner, Madison; Lee S. Zuriff, East Brunswick, all of N.J.

[73] Assignee: Warner-Lambert Company, Morris Plains, N.J.

[22] Filed: Mar. 7, 1975

[21] Appl. No.: 556,504

[52] U.S. Cl. .................. 195/103.5 R; 195/99; 195/101
[51] Int. Cl.² .................. C12K 1/04; G01N 33/00
[58] Field of Search .............. 195/103.5 R, 96, 99, 195/100, 101, 102

[56] References Cited
UNITED STATES PATENTS

| | | | |
|---|---|---|---|
| 3,790,447 | 2/1974 | Hirata et al. | 195/103.5 R |
| 3,834,991 | 9/1974 | Megraw et al. | 195/103.5 R |
| 3,881,993 | 5/1975 | Freake et al. | 195/103.5 R |

OTHER PUBLICATIONS

D. E. Leavelle et al. "Staphylococcal Clumping On Microtiter Plates" Am. J. Clin. Path. 55 pp. 452–457 (1971).

*Primary Examiner*—A. Louis Monacell
*Assistant Examiner*—C. A. Fan
*Attorney, Agent, or Firm*—Albert H. Graddis; Frank S. Chow; Anne M. Kelly

[57] ABSTRACT

An improved composition and method for detecting fibrinogen, fibrinogen split products and/or fibrin split products in blood comprises utilizing killed, dyed *Staphylococcus aureus* cells which can be prepared by either of two methods. In the first method, *Staphylococcus aureus* organisms are incubated in a nutrient medium containing a polyalkylene glycol having a molecular weight of from 1000 to 5000 to which is added triphenyltetrazolium chloride; the growing organisms reduce the triphenyltetrazolium chloride to triphenylformazan which imparts coloration to the cells; the dyed *Staphylococcus aureus* cells are killed and substantially all untrapped dye is removed. In an alternate method, a suspension of Fast Black Salt K is added to a suspension of killed *Staphylococcus aureus* cells, and the dyed cells which result are washed to remove substantially all unfixed dye. The killed, dyed *Staphylococcus aureus* cells prepared by either method are suspended in an imidazole buffer to maintain a pH of 7.4. The suspension may be lyophilized if desired. The determination of fibrinogen split products and/or fibrin split products in blood serum is performed by serially diluting the blood serum test sample and adding a specified volume of reconstituted killed, dyed *Staphylococcus aureus* cells to an equivalent volume of each serial dilution of serum test sample, and observing the serial dilutions for the presence of visible clumping as a positive test result. Coloration of the cells greatly improves visualization of the end point of the test. The concentration of fibrinogen split products and/or fibrin split products in the blood serum test sample can be calculated if a comparison test is run with a serum containing a known amount of fibrinogen, fibrinogen split products and/or fibrin split products.

35 Claims, No Drawings

COMPOSITION FOR DETECTING FIBRINOGEN, FIBRINOGEN SPLIT PRODUCTS AND FIBRIN SPLIT PRODUCTS

BACKGROUND OF THE INVENTION

1. Field of the Invention

The present invention relates to an improved composition and method for detecting fibrinogen, fibrinogen split products and/or fibrin split products in blood by utilizing a suspension of killed, dyed *Staphylococcus aureus* cells.

2. Description of the Prior Art

The determination of fibrinogen, fibrin split products and fibrinogen split products in blood using *Staphylococcus aureus* cells is known:

It has been shown that staphylococcal cells contain two types of coagulase: a free coagulase form and a bound coagulase form. The free coagulase causes clotting of fibrinogen when it is liberated into a culture medium. However, while the bound coagulase or clumping factor is not released from the bacterial cell and therefore cannot cause clotting, it will cause a "clumping" phenomenon in the presence of fibrinogen. This "clumping" phenomenon has not been definitely characterized but appears to be caused by a precipitation reaction or localized clotting of fibrin on the *Staphylococcus aureus* cell wall which results in "clumping". (Duthrie, E. S., J. Gen. Microbiol. 10: 427–436 (1954) and Duthrie, E. S., J. Gen. Microbiol. 13: 383–393 (1955).

Hawiger, J., et al., J. Lab. Clin. Med. 75: 93–108 (1970), disclosed that, of the two types of split products which are formed during fibrinogenolysis, only the early split products cause clumping with *Staphylococcus aureus* cells. The early split products include fibrin monomers, fibrinogen split products and fibrin split products which are formed as the first hydrolytic products resulting from the action of plasmin on fibrinogen or fibrin. The early split products are relatively large peptides, whereas the late split products, formed by continued hydrolysis of the early split products, are smaller peptides. Late fibrin split products and late fibrinogen split products do not cause clumping with *Staphylococcus aureus* cells. A slide test method as well as a tube test method for determining the staphylococcal clumping characteristics of the various split products formed during fibrinogenolysis are described by Hawiger et al.

Leavelle, D. E., et al., Am. J. Clin. Path. 55: 452–457 (April, 1971), proposed a modification of the method of Hawiger et al.: microtiter plates are used in order to serially dilute the serum test samples (as well as the fibrinogen standards) for the determination of fibrinogen, fibrin monomers and fibrinogen split products in blood by means of staphylococcal clumping characteristics.

SUMMARY OF THE INVENTION

This invention relates to an improved composition and method for detecting fibrinogen, fibrinogen split products and/or fibrin split products in blood by utilizing killed, dyed *Staphylococcus aureus* cells prepared by either of two methods: the first method comprises incubating *Staphylococcus aureus* organisms in a nutrient medium containing a polyalkylene glycol having a molecular weight of from 1000 to 5000 and adding a sufficient amount of triphenyltetrazolium chloride which can be reduced by the growing organisms to form colored triphenylformazan with the *Staphylococcus aureus* cells; the dyed *Staphylococcus aureus* cells are killed, and substantially all untrapped dye is removed; according to a second method, a suspension of Fast Black Salt K is added to a suspension of killed *Staphylococcus aureus* cells and the resultant dyed cells obtained are washed repeatedly to remove substantially all unfixed dye. The killed, dyed *Staphylococcus aureus* cells obtained by either method are suspended in an imidazole buffer to maintain a pH of about 7.4, and, optionally, lyophilized. The use of the killed, dyed *Staphylococcus aureus* cells for detecting fibrinogen, fibrinogen split products and/or fibrin split products provides a more readily visible end point for observation of the clumping phenomenon in serial dilutions of the serum test sample.

DESCRIPTION OF THE PARTICULAR EMBODIMENTS

It has now been found that when killed, dyed *Staphylococcus aureus* cells are used for the detection of fibrinogen split products and/or fibrin split products in blood, the end point, which is the point at which there is the least discernible clumping of cells, is more readily observable.

One type of dyed *Staphylococcus aureus* cells can be prepared by incubating *Staphylococcus aureus* organisms in a nutrient medium containing a suitable antifoam agent. Any aqueous nutrient medium which will sustain the growth of *Staphylococcus aureus* cells is suitable; preferably, Brain Heart Infusion Broth is used. The antifoam agent is necessary to prevent excessive foaming of the fermentation broth during the sparging aeration which is required to promote growth of the bacteria. It is important to select an antifoam agent which will not adversely affect the clumping characteristics of the *Staphylococcus aureus* cells. Furthermore, since the growing bacteria are to be dyed in a subsequent process step, it is mandatory that the selected antifoam agent also be compatible with the dye and with the production of clumping factor. It has now been found that a polyalkylene glycol having a molecular weight of from about 1000 to about 5000 which is only slightly soluble in water (less than 0.1 gram in 100 grams of water) fulfills both of the aforementioned requirements. Typically, the polyalkylene glycols having a molecular weight of from 1000 to 5000 can be selected from a group consisting of polypropylene glycol, polybutylene glycol and triols derived from propylene oxides. Preferably, the slightly soluble polyalkylene glycol is selected from the group consisting of polypropylene glycol and polybutylene glycol having a molecular weight from 1500 to 4000; most preferably, a slightly water soluble polypropylene glycol having a average molecular weight of about 2000 is used. A suitable commercially available material which is effective in the fermentation broth of this invention is DOW POLYGLYCOL P-2000 marketed by Dow Chemical Company, Midland, Mich.

In a typical fermentation broth, from about 0.003 to about 0.3 ml of polyalkylene glycol is used per liter of nutrient medium containing from about 0.1 to about 10 ml of a subculture of *Staphylococcus aureus*. Incubation of aforementioned fermentation broth is conducted from about 30° C to about 37° C for from about 4 to about 24 hours, with sparging aeration. In the preferred embodiment of this invention, 1 liter of a Bacto Brain Heart Infusion nutrient medium containing 0.03 ml of a polypropylene glycol having an average molecular weight of about 2000 is inoculated with 0.03 ml of a subculture of *Staphylococcus aureus;* incubation is conducted at from about 35° C to about 37° C for about 21 hours, with sparging aeration, but without mechanical stirring.

After a sufficient amount of *Staphylococcus aureus* bacteria have grown out, the cells are ready for dying. It is essential that the dye selected become thoroughly entrapped or fixed to the cells so that it cannot be removed by washing or standing in suspension. Further, the fixed or entrapped dye must not adversely affect the clumping characteristics of the killed *Staphylococcus aureus* cells. It has been found that triphenyltetrazolium chloride dyes (2,3,5-triphenyltetrazolium chloride, 2(p-iodophenyl)-3-(p-nitrophenyl)-5-phenyltetrazolium chloride and 3,3'-(3,3'-dimethoxy-4,4'-biphenylene)bis[2,5-diphenyl-2H-tetrazolium chloride) are suitable for dying the *Staphylococcus aureus* bacteria cells to be used in the practice of this invention. Of these, 2,3,5-triphenyltetrazolium chloride is preferred. The growing *Staphylococcus aureus* bacteria actually metabolize and reduce the soluble, colorless triphenyltetrazolium chloride to corresponding insoluble, colored triphenylformazan, thereby imparting coloration to the *Staphylococcus aureus* cells. Typically, a saline solution of from about 0.01 grams to about 1 gram of a triphenyltetrazolium chloride dye is added to a 1 liter fermentation containing the polyalkylene glycol and *Staphylococcus aureus* bacteria as described above; preferably, about 5 ml of a saline suspension containing about 0.3 grams of triphenyltetrazolium chloride is added to the fermentation broth. Incubation of the dye-containing fermentation broth is continued for from about 0.5 to about 5 hours at a temperature of from about 30° C to about 37° C; preferably, continuing the incubation for about 2 hours at from about 35° C to about 37° C is sufficient to permit reduction to the water-insoluble dye and coloration of the *Staphylococcus aureus* cells.

Next, the fermentation broth containing the dyed *Staphylococcus aureus* cells is heated to at least 70° C for at least 3 hours to kill substantially all the dyed *Staphylococcus aureus* cells. This heating reaction may be conducted at a higher temperature for longer periods of time, if desired, in order to be sure that all of the dyed *Staphylococcus aureus* cells have been killed. A small amount of the dyed, heat-killed cells may be grown out on a Trypticase Soy Agar Plate in order to be sure that substantially all dyed cells have been killed.

The heat-killed, dyed *Staphylococcus aureus* cells as described above are separated from the nutrient medium by centrifugation, washed with distilled water until substantially all untrapped dye has been removed. The purified dyed cells are then re-suspended in an 0.017M aqueous imidazole buffer solution for utilization in the improved test method of this invention.

In the alternate method for preparing dyed cells suitable for use in the improved clumping test of this invention, killed *Staphylococcus aureus* cells are dyed with Fast Black Salt K. Fast Black Salt K, which is a diazo salt of 2,5-dimethoxy-4-[(4-p-nitrophenyl)azo]benzenamine, has been found to have a high degree of fixation to the killed cells and is not easily washed out either during purification techniques or, subsequently, upon standing in suspension, prior to use in the clumping test. More importantly, the fixed dye does not destroy the clumping characteristics of the *Staphylococcus aureus* cells: killed cells dyed with Fast Black Salt K have been found to remain sensitive to fibrinogen, fibrinogen split products and/or fibrin split products after dying. In order to achieve maximum dye fixation, an aqueous imidazole buffer suspension of killed *Staphylococcus aureus* cells, containing from about 3 to about 4 mg of cells per milliliter of suspension, is contacted with an aqueous imidazole buffer solution of Fast Black Salt K, containing from about 3 to about 4 mg of Fast Black Salt K per milliliter of solution. The killed, dyed cells obtained are washed with distilled water once and then washed with a 4% bovine serum albumin solution to remove substantially all unfixed dye. After the final centrifugation, the purified dyed cells are re-suspended in an 0.017M aqueous imidazole buffer solution for utilization in the improved test method of this invention.

In terms of stability and marketability, a lyophilized form of the novel dyed cell/buffer composition of this invention is preferred rather than the above-described suspension. However, lyophilization techniques are not successful with the cells suspended in 0.017M imidazole buffer since the weight of the solid material present in the 0.017M cell/buffer suspension is not sufficient to undergo lyophilization. It has been found that by increasing the concentration of cells and buffer in the suspension prior to lyophilization, a lyophilized cake can be prepared which can be reconstituted with an additional volume of distilled water to provide the required concentration of material necessary for use in the improved clumping test of this invention. For example, it has been found that at least triple the concentration of cell/buffer suspension required for the *Staphylococcus aureus* clumping test of this invention can be readily lyophilized and reconstituted with distilled water in amount equal to triple the initial volume of the suspension. Higher concentrations of cell/buffer suspension could also be lyophilized but would provide, after reconstitution, too great a volume of test reagent to be utilized at one time under actual laboratory testing conditions. Storage of the liquid dyed cell/buffer suspension is not recommended.

In practice, concentrated dyed cell/buffer suspensions are prepared and lyophilized in bulk or in vials containing test aliquots. Alternately, the prepared concentrated suspension can be diluted with distilled water to provide the required amounts of dyed cells and buffer for use directly in the improved clumping test of this invention.

Typically, the purified, killed, dyed *Staphylococcus aureus* cells prepared by either of the above-described procedures are suspended in an 0.051M aqueous imidazole buffer (pH about 7.4) in a ratio of from about 7.5 milligrams to about 12 milligrams of dyed cells per milliliter of buffer. Preferably, 9 mg/ml are used in the 0.051M buffer, pH about 7.4. The above-described concentrated suspension may be diluted with distilled water to provide from about 1.5 to about 6 mg/ml, preferably about 3 mg/ml of dyed *Staphylococcus aureus* cells in the 0.017M imidazole buffer (pH about 7.4) which is most preferably used in running the improved clumping test directly. If the 0.051M buffer suspension of dyed *Staphylococcus aureus* cells is frozen and lyophilized, it is reconstituted with an amount of distilled water equivalent to three times the initial volume of the dyed cell suspension prior to lyophilization.

The improved *Staphylococcus aureus* clumping test of this invention will indicate the presence of fibrinogen, fibrinogen split products and/or fibrin split products in blood plasma. However, in a clinical situation, the test is used to determine levels of fibrinogen split products and/or fibrin split products in blood serum. (Serum preparation involves the removal of fibrinogen by clotting of the plasma). The presence of abnormal levels of fibrinogen split products and/or fibrin split products in blood serum is indicative of intravascular coagulation and related disease states.

For the determination of fibrinogen split products or fibrin split products in blood serum, an 0.017M imidazole buffer, pH about 7.4, is used to serially dilute the blood serum test sample. This buffer is prepared by dissolving about 0.69 grams of imidazole in about 580 ml of distilled water; the pH is adjusted to 7.4 ± 0.05 with 0.1M HCl, and the solution is brought to a volume of 600 ml with the distilled water; the pH is again adjusted to 7.4 to provide a 0.017M buffer. An anti-bacterial agent such as Thimerosal, may be added to the buffer solution to prevent the growth of micro-organisms. To run the test, a specified amount, preferably 50 μl, of 0.017M imidazole buffer solution is added to each well of a microtiter plate containing seven or more wells. Serial dilutions of blood serum test sample are made in each well using a microtiter diluter, preferably a 50 μl microtiter diluter. An amount of dyed *Staphylococcus aureus* cell suspension (containing either entrapped reduced tetrazolium chloride or "fixed" Fast Black Salt K dye in an 0.017M imidazole buffer) equivalent to the initial amount of imidazole buffer (preferably 50 μl) is added to each well of the microtiter plate and the plate is placed on a shaker plate or intermittently shaken by hand. After about 10 minutes, the microtiter plate is observed for the presence of clumping. The end point is read as the well containing the least discernible clumping of cells visible to the unaided eye. The concentration of fibrin split products and fibrinogen split products in the blood serum test sample is calculated by comparison of test results with a standard solution containing a known amount fibrinogen, fibrin split products or fibrinogen split products. In actual practice the fibrinogen standard is generally used and the quantity of split products per milliliter of blood serum is expressed in terms of fibrinogen equivalents (μg fibrinogen/ml).

*Staphylococcus aureus* cells dyed with a tetrazolium chloride dye provide a test which is as sensitive as the known, undyed staphylococcus clumping test (0.62 μg/ml of split products can be detected in blood serum). *Staphylococcus aureus* cells dyed with Fast Black Salt K can detect 1.25 μg of split products per milliliter of blood serum. The tetrazolium chloride-dyed *Staphylococcus aureus* cells are preferred (especially those dyed with 2,3,5-triphenyltetrazolium chloride) since a more sensitive test results. However, inasmuch as the normal range of split products in blood serum is 0 to 10 μg/ml, tests performed with the Fast Black Salt K dyed cells are more than sufficiently sensitive to detect abnormal levels of split products in blood serum.

The improved, dyed *Staphylococcus aureus* clumping test method of this invention is reproducible, sensitive and easy to perform. End points can be read accurately and multiple samples can be analyzed simultaneously in approximately 30 minutes.

In order to further illustrate the practice of the invention, the following examples are included:

EXAMPLE 1

Preparation of Dyed Staphylococcus aureus

To 3 liters of a fermentation of Bacto Brain Heart Infusion broth and *Staphylococcus aureus*, is added 0.1 ml of DOW POLYGLYCOL P-2000 and incubation is conducted at 35° C to 37° C for 21 hours with sparging aeration. A solution of 0.9 grams of 2,3,5-triphenyltetrazolium chloride in 5 ml of sodium chloride (U.S.P.) is added to the fermentation broth and the incubation is continued for an additional 2 hours, with vigorous stirring. The fermentation is then heated to a temperature of 70° C ± 1° C, and held at this temperature with constant stirring for 3 hours to kill substantially all of the dyed *Staphylococcus aureus* cells. The heat-killed dyed cells are centrifuged, and the supernatant liquid is discarded. The sediment is re-suspended in 1.5 liters of sodium chloride solution, (U.S.P.) and the bacterial suspension obtained is centrifuged. The supernatant liquid is again discarded and the dyed cells obtained are re-suspended in 1.5 liters of distilled water. Centrifugation and re-suspension as above are repeated for a total of 4 washes to remove substantially all untrapped dye.

EXAMPLE 2

Preparation of Buffer 0.69 grams of imidazole are dissolved in about 580 ml of distilled water. The pH is adjusted to 7.4 ± 0.05 with 0.1M HCl. The solution is brought to a volume of 600 ml with distilled water and the pH is again adjusted to 7.4, if necessary, with 0.1M HCl, to provide an 0.017M buffer.

EXAMPLE 3

Preparation of Lyophilized Dyed Staphylococcus Aureus Cells 1.8 grams of the washed cell sediment from Example 1 are re-suspended in 200 ml of 0.051M imidazole buffer, pH 7.4. One ml aliquots of this suspension are placed into 3 ml vials. The vials are frozen in the lyophilizer and then lyophilized until dry. The lyophilized dyed *Staphylococcus aureus* cells are stored at 4° C.

EXAMPLE 4

Determination of Fibrin Split Products and/or Fibrinogen Split Products in Blood Serum One vial from Example 3 containing the lyophilized, dyed *Staphylococcus aureus* cells in imidazole buffer is reconstituted with 3 ml of distilled water to provide cells suspended in 0.017M imidazole buffer. 50 μl of imidazole buffer of Example 2 are added to each well of a microtiter plate containing seven wells. Seven serial dilutions of the blood serum test sample are then made using a 50 μl microtiter diluter. 50 μl of the reconstituted, dyed *Staphylococcus aureus* cells are added to the serial dilutions in each well of the microtiter plate and the plate is intermittently shaken by hand. After 10 minutes, the microtiter plate is observed for the presence of clumping. The end point is read as the well containing the least discernible clumping of cells visible to the unaided eye. The concentration of fibrinogen split products and/or fibrin split products in the blood serum test sample is calculated by comparison of test results with a standard solution containing a known amount of fibrinogen, fibrinogen split products or fibrin split products. The test serum exhibited an end point in the sixth well, equivalent to a titer of 1:64. The fibrinogen standard containing 10 μg/ml had a fourth well end point. The concentration of split products can be calculated as follows:

10 μg/ml/16 = 0.625 μg/ml
0.625 μg/ml × 64 = 40 μg split products/ml (fibrinogen equivalent)

EXAMPLE 5

Preparation of Dyed *Staphylococcus aureus*

18 mg of Fast Black Salt K are added to 18 ml of an 0.017M imidazole buffer, and the final pH is adjusted to 7.4. This dye/buffer solution is added to 6 ml of an 0.017M imidazole buffer suspension containing 18 mg of killed *Staphylococcus aureus* cells. The dyed cells obtained are centrifuged, washed with distilled water once and washed three times with a 4% bovine serum albumin solution. After final centrifugation, the resulting 18 mg of dyed cells are suspended in 2 ml of 0.051M imidazole buffer and the pH is adjusted to 7.4. One ml of this suspension is placed into 3 ml vials. The vials are frozen in a lyophilizer and lyophilized until dry. The lyophilized, dyed *Staphylococcus aureus* cells are stored at 4° C.

EXAMPLE 6

Determination of Fibrinogen, Fibrin and Fibrinogen Split Products In Blood Serum One vial from Example 5 containing lyophilized, *Staphylococcus aureus* cells dyed with Fast Black Salt K in imidazole buffer is reconstituted with 3 ml of distilled water to provide cells suspended in 0.017M imidazole buffer. 50 μl of the imidazole buffer of Example 2 is added to each well of a microtiter plate containing seven wells. Serial dilutions of blood serum test sample are prepared using a 50 μl microtiter diluter. 50 μl of the reconstituted, dyed *Staphylococcus aureus* cells is added to each of the serial dilutions in each well of the microtiter plate and the plate is intermittently shaken by hand. After 10 minutes, the microtiter plate is observed for the presence of clumping. The test serum exhibited an end point in the sixth well, equivalent to a titer of 1:64. The fibrinogen standard containing 10 μg/ml had a third well end point. The concentration of split products can be calculated as follows:

10 μg/ml/8 = 1.25 μg/ml
(1.25 μg/ml) (64) = 80 μg/ml

We claim:
1. A composition suitable for determining fibrinogen, fibrin split products and fibrinogen split products in blood which comprises a buffer suspension of dyed *Staphylococcus aureus* cells prepared by:
  A. inoculating a suitable nutrient medium containing a polyalkylene glycol having a molecular weight of from about 1000 to about 5000, with a subculture of *Staphylococcus aureus* cells;
  B. incubating (A) at from about 30° C to about 37° C for from about 4 to about 24 hours, with sparging aeration;
  C. adding a saline suspension of a triphenyltetrazolium chloride dye to (B) and continuing the incubation for from about 0.5 to about 5 hours until a sufficient amount of the triphenyltetrazolium chloride is reduced to triphenylformazan to impart coloration to the *Staphylococcus aureus* cells;
  D. heating (C) to at least 70° C for at least 3 hours, to kill substantially all the dyed *Staphylococcus aureus* cells;
  E. separating the heat-killed dyed cells of (D) from the nutrient medium and washing to remove substantially all untrapped dye; and
  F. suspending the killed, dyed cells in a buffer solution which will maintain a pH of about 7.4.

2. A composition according to claim 1 wherein, in Step C, the incubation is conducted for about 2 hours.

3. A composition according to claim 2 wherein the polyalkylene glycol is slightly soluble in water and is selected from the group consisting of polypropylene glycol, polybutylene glycol and triols derived from propylene oxides, having a molecular weight of 1500 to 4000.

4. A composition according to claim 3 wherein the polyalkylene glycol is a polypropylene glycol having an average molecular weight of about 2000.

5. A composition according to claim 4 wherein the buffer solution is a 0.017M imidazole buffer.

6. A lyophilized composition of claim 1.

7. A lyophilized composition of claim 4.

8. A composition according to claim 4 wherein the buffer solution is a 0.051 M imidazole buffer.

9. A lyophilized composition of claim 8.

10. A composition for determining fibrinogen, fibrin split products and fibrinogen split products in blood which comprises an aqueous suspension of dyed *Staphylococcus aureus* cells prepared by:
  A. inoculating about 1 liter of a brain heart infusion nutrient medium containing about 0.03 ml of a polypropylene glycol having an average molecular weight of about 2000, with about 0.03 ml of a subculture of *Staphylococcus aureus*;
  B. incubating (A) at about 35° C to about 37° C for about 21 hours, with sparging aeration;
  C. adding 5 ml saline suspension containing 0.3 g of 2,3,5-triphenyltetrazolium chloride to (B) and continuing the incubation for about 2 hours to reduce 2,3,5-triphenyltetrazolium chloride to 1,3,5-triphenylformazan and impart coloration to the *Staphylococcus aureus* cells;
  D. heating (C) at about 70° C for about 3 hours to kill substantially all of the dyed *Staphylococcus aureus* cells;
  E. separating the heat-killed, dyed cells of (D) from the nutrient medium and washing to remove substantially all untrapped dye; and
  F. suspending about 9 mg. of washed, killed, dyed cells of (E) in about 1 ml of 0.051M imidazole buffer to maintain the suspension at a pH of about 7.4.

11. A lyophilized composition of claim 10.

12. A lyophilized composition of claim 10.

13. A method for preparing dyed *Staphylococcus aureus* cells suitable for use in the determination of the presence of fibrinogen, fibrin split products and fibrinogen split products in blood which comprises:
  A. inoculating a suitable nutrient medium containing a polyalkylene glycol having a molecular weight of from about 1000 to about 5000, with a subculture of *Staphylococcus aureus* cells;
  B. incubating (A) at from about 30° C to about 37° C for from about 4 to about 24 hours, with sparging aeration;

C. adding a saline suspension of a triphenyltetrazolium chloride dye to (B) and continuing the incubation for from about 0.5 to about 5 hours until a sufficient amount of the triphenyltetrazolium chloride is reduced to triphenylformazan to impart coloration to the *Staphylococcus aureus* cells;

D. heating (C) to at least 70° C for at least 3 hours, to kill substantially all the dyed *Staphylococcus aureus* cells;

E. separating the heat-killed dyed cells of (D) from the nutrient medium and washing to remove substantially all untrapped dye; and F. suspending the killed, dyed cells in a buffer solution which will maintain a pH of about 7.4.

14. A method according to claim 13 wherein, in Step C, the incubation is conducted for about 2 hours.

15. A method according to claim 14 wherein the polyalkylene glycol is slightly soluble in water and is selected from the group consisting of polypropylene glycol, polybutylene glycol and triols derived from propylene oxides, having a molecular weight of 1500 to 4000.

16. A method according to claim 15 wherein the polyalkylene glycol is a polypropylene glycol having an average molecular weight of about 2000.

17. A method according to claim 16 wherein the buffer solution is a 0.051M imidazole buffer.

18. A method according to claim 13 wherein, in an additional step, the suspension of killed, dyed cells is lyophilized.

19. A method according to claim 16 wherein, in an additional step, the suspension of killed, dyed cells is lyophilized.

20. A method according to claim 17 wherein, in an additional step, the suspension of killed, dyed cells is lyophilized.

21. A composition suitable for determining fibrinogen, fibrin split products and fibrinogen split products in blood which comprises a buffer suspension of killed, dyed *Staphylococcus aureus* cells prepared by:

A. inoculating a suitable nutrient medium containing a polyalkylene glycol having a molecular weight of from about 1000 to about 5000, with a subculture of *Staphylococcus aureus* cells;

B. incubating (A) at from about 30° C to about 37° C for from about 4 to about 24 hours, with sparging aeration;

C. heating (B) to at least 70° C for at least 3 hours, to kill substantially all the *Staphylococcus aureus* cells;

D. separating the heat killed cells of (C) from the nutrient medium;

E. suspending the killed, separated cells of (D) in a buffer solution which will maintain a pH of about 7.4.

F. contacting (E) with an aqueous buffer solution of Fast Black Salt K dye for a time sufficient to impart coloration to the *Staphylococcus aureus* cells;

G. washing the killed, dyed cells of (F) to remove substantially all unfixed Fast Black Salt K dye; and H. re-suspending the killed, dyed cells of (G) in a buffer solution which will maintain a pH of about 7.4.

22. A composition according to claim 21 wherein the polyalkylene glycol is slightly soluble in water and is selected from the group consisting of polypropylene glycol, polybutylene glycol and triols derived from propylene oxides, having a molecular weight of 1500 to 4000.

23. A composition according to claim 22 wherein the polyalkylene glycol is a polypropylene glycol having an average molecular weight of about 2000.

24. A composition according to claim 23 wherein the buffer solution is a 0.017M imidazole buffer.

25. A composition according to claim 23 wherein the buffer solution is a 0.051 M imidazole buffer.

26. A lyophilized composition of claim 21.

27. A lyophilized composition of claim 22.

28. A lyophilized composition of claim 25.

29. A composition for determining fibrinogen, fibrin split products and fibrinogen split products in blood which comprises an aqueous suspension of dyed *Staphylococcus aureus* cells prepared by:

A. inoculating about 1 liter of a brain heart infusion nutrient medium containing about 0.03 ml of a polypropylene glycol having an average molecular weight of about 2000, with about 0.03 ml of a subculture of *Staphylococcus aureus;*

B. incubating (A) at about 35° C to about 37° C for about 21 hours, with sparging aeration;

C. heating (B) at about 70° C for about 3 hours to kill substantially all of the *Staphylococcus aureus* cells;

D. separating the heat-killed cells of (C) from the nutrient medium;

E. suspending about 18 mg. of killed, separated cells of (D) in about 6 ml of 0.017 M imidazole buffer to maintain the suspension of a pH of about 7.4;

F. contacting (E) with about 18 ml. of an 0.017 M imidazole buffer containing about 18 mg. of Fast Black Salt K dye for a time sufficient to impart coloration of the *Staphylococcus aureus* cells;

G. washing the killed, dyed cells of (E) to remove substantially all unfixed dye; and H. re-suspending about 9 mg. of the washed, killed, dyed cells of (G) in about one ml. of 0.051 M imidazole buffer to maintain the suspension at a pH of about 7.4.

30. A method for the determination of fibrin split products and fibrinogen split products in blood serum which comprises:

A. adding a specified amount of an imidazole buffer to each well of a microtiter plate;

B. adding an amount equivalent to the amount of (A) of blood serum test sample to the first well of the microtiter plate of (A) and serially diluting, using a microtiter diluter;

C. adding an amount equivalent to the amount of (A), of the dyed *Staphylococcus aureus* cell suspension of claim 1 to each well of the microtiter plate of (B); and D. observing the wells of (C) for visible clumping of the *Staphylococcus aureus* cells as a positive indication of the presence of fibrin split products and fibrinogen split products in the test blood serum.

31. A method according to claim 30 wherein, in Steps (A) and (C), a 0.017M imidazole buffer is used.

32. A method according to claim 30 wherein, in Step (B), seven serial dilutions are carried out.

33. A method for the determination of fibrin split products and fibrinogen split products in blood serum which comprises:

A. adding a specified amount of an imidazole buffer to each well of a microtiter plate;

B. adding an amount equivalent to the amount of (A) of blood serum test sample to the first well of the microtiter plate of (A) and serially diluting, using a microtiter diluter;

C. adding an amount equivalent to the amount of (A), of the dyed *Staphylococcus aureus* cell suspension of claim 21 to each well of the microtiter plate of (B); and D. observing the wells of (C) for visible clumping of the *Staphylococcus aureus* cells as a positive indication of the presence of fibrin split products and fibrinogen split products in the test blood serum.

34. A method according to claim 33 wherein, in Steps (A) and (C), an 0.017 M imidazole buffer is used.

35. A method according to claim 33 wherein, in Step (B), seven serial dilutions are carried out.

* * * * *

UNITED STATES PATENT OFFICE
CERTIFICATE OF CORRECTION

Patent No. 3,990,947　　　　　　　　　Dated NOVEMBER 9, 1976

Inventor(s) JAMES R. BUTLER, WALTER E. JACOBSON, DONALD PAUL KRONISH, JAMES E. TURNER and LEE S. ZURIFF It is certified that error appears in the above-identified patent and that said Letters Patent are hereby corrected as shown below:

Column 8, in Claim 12, Line 57, "Claim 10", should read ---Claim 29---.

Signed and Sealed this

Twenty-first Day of March 1978

[SEAL]

Attest:

RUTH C. MASON
Attesting Officer

LUTRELLE F. PARKER
Acting Commissioner of Patents and Trademarks